US00PP23056P2

(12) United States Plant Patent
Klemm et al.

(10) Patent No.: US PP23,056 P2
(45) Date of Patent: Sep. 18, 2012

(54) ***SCAEVOLA* PLANT NAMED 'KLESC10728'**

(50) Latin Name: *Scaevola aemula*
Varietal Denomination: KLESC10728

(75) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 28 days.

(21) Appl. No.: 13/065,819

(22) Filed: Mar. 29, 2011

(51) Int. Cl.
*A01H 5/00* (2006.01)

(52) U.S. Cl. ..... Plt./363

(58) Field of Classification Search ..... Plt./363
See application file for complete search history.

*Primary Examiner* — Susan McCormick Ewoldt

(74) *Attorney, Agent, or Firm* — Jondle & Associates, P.C.

(57) ABSTRACT

A *Scaevola* plant named 'KLESC10728' particularly distinguished by light violet-blue flowers, good branching, good flower quality, and medium early flowering, is disclosed.

1 Drawing Sheet

Genus and species: *Scaevola aemula.*
Variety denomination: 'KLESC10728'.

BACKGROUND OF THE NEW PLANT

The present invention comprises a new and distinct variety of *Scaevola*, botanically known as *Scaevola aemula* and hereinafter referred to by the variety name 'KLESC10728'. 'KLESC10728' was discovered in June 2006 in Stuttgart, Germany and originated from an open pollination between the proprietary female parent 'SC 060016' (unpatented) and an unknown male parent. A single plant selection was subsequently chosen for further evaluation and asexual propagation.

The new variety was first propagated via vegetative cuttings and invitro propagation in May 2007 in Stuttgart, Germany and has been asexually reproduced repeatedly by vegetative cuttings in Stuttgart, Germany for more than 10 generations. 'KLESC10728' has been found to retain its distinctive characteristics through successive asexual propagations via vegetative cuttings.

Plant Breeder's Rights for this variety have not been applied for. 'KLESC10728' has not been made publicly available more than one year prior to filing of this application.

SUMMARY OF THE INVENTION

The following are the most outstanding and distinguishing characteristics of the new variety when grown under normal horticultural practices in Stuttgart, Germany.

1. Light violet-blue flowers;
2. Good branching;
3. Good flower quality; and
4. Medium early flowering.

DESCRIPTION OF THE PHOTOGRAPHS

This new *Scaevola* plant is illustrated by the accompanying photograph which shows inflorescences and foliage of the plant. The colors shown are as true as can be reasonably obtained by conventional photographic procedures. The photograph was taken in the Spring of 2010 of a plant about 3 months old and grown from rooted cuttings in 10 centimeter pots in a glass greenhouse in Stuttgart, Germany under normal horticultural practices.

DESCRIPTION OF THE NEW VARIETY

The following detailed descriptions set forth the distinctive characteristics of 'KLESC10728'. The data which define these characteristics were collected from asexual reproductions carried out in Stuttgart, Germany. The plant history was taken in the Spring of 2010 on 3-month old plants grown in 10 centimeter pots in a glass greenhouse. The plants were pinched once at 9 weeks. The color readings were determined under natural light. Color references are primarily to The R.H.S. Colour Chart of The Royal Horticultural Society of London (R.H.S.), Fifth Edition (2007).

DETAILED BOTANICAL DESCRIPTION

Classification:
- *Family.*—Goodeniaceae.
- *Botanical.*—*Scaevola aemula.*
- *Common name.*—Fan flower.

Parentage:
- *Female parent.*—The proprietary female Scaevola plant 'SC 060016' (unpatented).
- *Male parent.*—Unknown.

Growth:
- *Form.*—Flat.
- *Growth and branching habit.*—Flat.
- *Height (measured from the top of the soil).*—7.0 cm.
- *Width (horizontal plant diameter).*—20.0 cm.
- *Plant spread (from the base to the stem tips, including the flowers).*—7.0 cm.
- *Time to produce a finished flowering plant.*—12 weeks.
- *Outdoor plant performance and use.*—Heat resistant, sun-loving plants used for mixed baskets.
- *Time to initiate and develop roots.*—4 weeks.
- *Root description.*—Fine, pale to white roots, moderate density.

Stems:
- *Length.*—8.0 cm to 12.0 cm.
- *Texture.*—Smooth.

Leaves:

*Arrangement*.—Alternate; the smaller leaves on the flowering stems are roughly at right angles to each other.

*Color*.—Immature and mature leaves: Upper surface: Between RHS 141A and RHS 137B. Lower surface: RHS 138B.

*Length*.—4.0 cm to 6.0 cm.

*Width*.—2.0 cm to 2.5 cm.

*Shape*.—Elliptical.

*Apex*.—Obtuse.

*Base*.—Acute.

*Margin*.—Serrate.

*Texture*.—Pubescent.

*Venation*.—Present.

*Venation color*.—RHS 142B.

Flower buds:

*Shape*.—Lanceolate.

*Length*.—Approximately 1.5 cm.

*Diameter*.—Approximately 0.2 cm.

Inflorescence:

*Blooming habit*.—Continuously from the Spring through the Fall.

*Lastingness of individual blooms on the plant*.—5 to 7 days.

*Fragrance*.—Absent.

*Inflorescence type*.—Raceme.

*Flower shape*.—Semi-circular or fan-like arrangement to form a lower part which is open tube-shaped.

*Pedicels*.—None, flowers are sessile.

Flowers:

*Flower diameter*.—2.0 cm to 3.0 cm.

*Flower depth*.—Approximately 1.5 cm.

*Flower tube*.—Shape: Ovate. Tube length: Approximately 1.0 cm.

*Petals*.—Number: 5, fused at base at obtuse angles with minimal overlap. Shape: Oblong. Apex: Fused. Base: Entire. Margin: Smooth. Texture: Smooth. Color: Mature: Upper surface: RHS 84A.

*Sepals*.—General: Composed of one larger and somewhat fleshy sepal and two narrow sepals at the base of the flower.

Reproductive organs:

*Stamen*.—Quantity: 5. Pollen amount: Moderate.

*Pistil*.—Quantity: 1 per flower.

COMPARISON WITH PARENTAL AND COMMERCIAL VARIETIES

'KLESC10728' differs from the female parent, 'SC 060016' (unpatented), in that 'KLESC10728' has light violet blue flowers that flower medium early, while 'SC 060016' has white flowers that flower early.

'KLESC10728' differs from the commercial variety, 'Brilliant' (unpatented), in that 'KLESC10728' has a lighter flower color than 'Brilliant'.

We claim:

1. A new and distinct variety of *Scaevola* plant named 'KLESC10728' as shown and described herein.

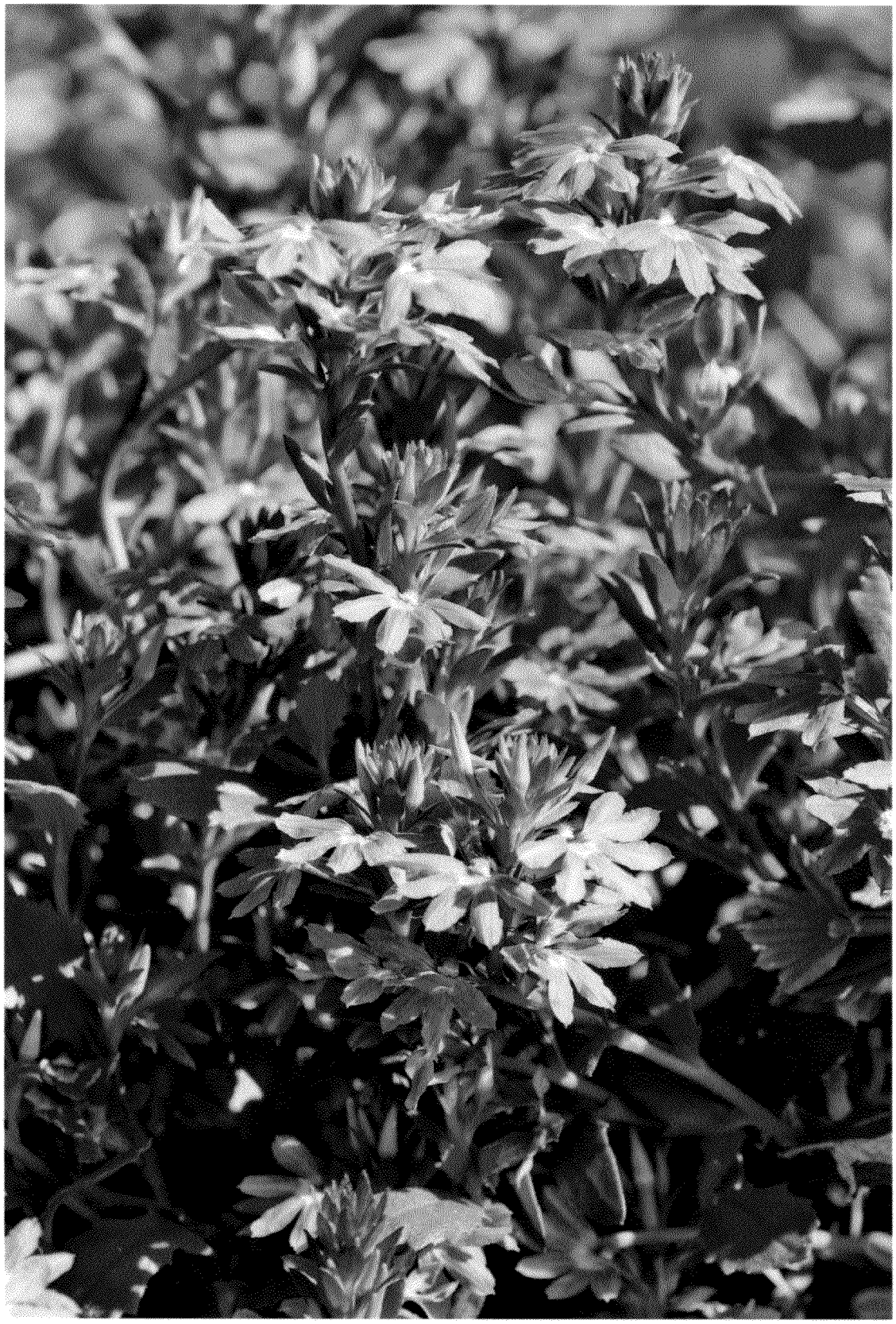

* * * * *